(12) United States Patent
Kapranov et al.

(10) Patent No.: US 11,898,200 B2
(45) Date of Patent: Feb. 13, 2024

(54) METHOD FOR DETECTING SINGLE STRAND BREAKS IN DNA

(71) Applicant: Huaqiao University, Fujian (CN)

(72) Inventors: Philipp Kapranov, Fujian (CN); Huifen Cao, Fujian (CN); Lorena Salazar-García, Fujian (CN); Fan Gao, Fujian (CN); Dongyang Xu, Fujian (CN); Ye Cai, Fujian (CN); Xueer Han, Fujian (CN); Fang Wang, Fujian (CN); Lu Tang, Fujian (CN)

(73) Assignee: Huaqiao University, Fujian (CN)

( * ) Notice: Subject to any disclaimer, the term of this patent is extended or adjusted under 35 U.S.C. 154(b) by 607 days.

(21) Appl. No.: 17/014,322

(22) Filed: Sep. 8, 2020

(65) Prior Publication Data

US 2021/0071233 A1    Mar. 11, 2021

(30) Foreign Application Priority Data

Sep. 5, 2019    (CN) .......................... 201910837092.1

(51) Int. Cl.
*C12Q 1/686* (2018.01)
*C12Q 1/6827* (2018.01)

(52) U.S. Cl.
CPC ........... *C12Q 1/686* (2013.01); *C12Q 1/6827* (2013.01)

(58) Field of Classification Search
CPC .... C12Q 1/686; C12Q 1/6806; C12Q 1/6869; C12Q 1/6827
See application file for complete search history.

(56) References Cited

U.S. PATENT DOCUMENTS

2018/0320190 A1    11/2018    Beetham et al.

FOREIGN PATENT DOCUMENTS

| CN | 105143525 A | 12/2015 |
| CN | 105754995 A | 7/2016 |
| CN | 108300765 A | 7/2018 |
| CN | 108753939 A | 11/2018 |

OTHER PUBLICATIONS

Biernacka et al., Communications biology, 1:181, 1-9, Oct. 2018.*
"DNA Damage, Aging, and Cancer"; Oct. 2009; Jan H.J. Hoeijmakers; The New England Journal of Medicine, Molecular Origins of Cancer, pp. 1475-1485.
"The DNA-Damage Response in Human Biology and Disease"; Oct. 2009; Stephen P. Jackson and Jiri Bartek; Nature, vol. 461/22, pp. 1071-1078.
"Single-Strand Break Repair and Genetic Disease"; Aug. 2008; Keith W. Caldecott; Nature Reviews/Genetics, vol. 9, pp. 619-631.
"Single-Strand Interruptions in Replicating Chromosomes Cause Double-Strand Breaks"; Jul. 2001; Andrei Kuzminov; Proceedings of the National Academy of Sciences of the United States of America, vol. 98, No. 15 pp. 8241-8246.
"Single-Stranded Breaks in DNA but Not Oxidation DNS Base Damages Black Transcriptional Elongation by RNA Polymerase II HeLa Cell Nuclear Extracts", Apr. 2004; Scott D. Kathe, Guang-Ping Shen and Susan S. Wallace; The Journal of Biological Chemistry, vol. 279, No. 18, pp. 18511-18520.
"Blockage of RNA Polymerase as a Possible Trigger for u.v. Light-Induced Apoptosis"; Mar. 1996; Mats Ljungman and Fenfen Zhang; Oncogene; pp. 823-831.
"Inhibition of RNA Polymerase II as a Trigger for the p53 Response"; 1999; Mats Ljungman, Fenfen Zhang, Feng Chen, Andrew J. Rainbow and Bruce C. McKay; Oncogene; 10 pgs.
"DNA Strand Break Repair and Neurodegeneration"; 2013; Stuart L. Rulten and Keith W. Coldecott; DNA Repair, vol. 12, Issue 8, 10 pgs.
"Nucleotide-Resolution DNA Double-Strand Break Mapping by Next-Generation Sequencing" Apr. 2013; Nicola Corsetto, Abhishek Mitra, Maria Joao Silva, Magda Bienco, Norbert Dojer, Qi Wang, Elif Karaca, Roberto, Chiarle, Magdalena Skrzypczak, Krzysztol Finalski, Philippe Pasero, Maga Rowicka and Ivan Dikic; Nature Methods, vol. 10, No. 4, 8 pgs.
"Bliss is a Versatile and Quantitative Method for Genome-Wide Profiling of DNA Double-Strand Breaks": Jan. 2017, Winston X. Yan, Reza Mrzazadeh, Silvano Garnerone, David Scott. Martin W. Schneider, Tomasz Kallas, Joaquin Custodio, Erik Warnersson, Yinqing Li, Linyi Gao, Yana Federova, Bernd Zetsche, Feng Zhang, Magda Lienco and Nicol Crosetto, Nature Communications, 9 pgs.
"Recent Advancements in DNA Damage-Transcription Crosstalk and High-Resolution Mapping of DNA Breaks"; 2017, Valerio Vitelli, Alessandro Galbiati, Fabio Iannelli, Fabio Pessina, Sheetal Sharma and Fabrizio D'Adda' Di Fagagna, Annual Review of Genomics and Human Genetics, pp. 87-113.
"DNA Break Mapping Reveals Topoisomerase II Activity Genome-Wide"; 2014; Laura Baranello, Fedor Kouzine, Damian Wojtowica, Kairong Cui, Teresa M Przytycka, Keji Zhao and David Levens; International Journal of Molecular Sciences, 13 pgs.
"Genome-Wide Analysis of Human Global and Transcription-Coupled Excision Repair of UV Damage at Single-Nucleotide Resolution" Feb. 2015; Jinchuan Hu, Sheera Adar, Chrisopher P. Selby, Jason D. Lieb and Aziz Sancar; Genes and Development, 14 pgs.

(Continued)

*Primary Examiner* — Cynthia B Wilder
(74) *Attorney, Agent, or Firm* — Cooper Legal Group LLC (57) ABSTRACT

The present disclosure discloses a method for detecting single strand breaks (SSBs) in DNA based on the following steps. First, DNA of interest is fragmented with a method that generates 3' ends that cannot be tailed. Second, the available 3' ends of the fragmented DNA corresponding to the pre-existing breaks are tailed. Third, SSBs are captured and their positions are identified genome-wide based on the following steps: (1) the tailed fragments are linearly amplified using a chimeric 5'-DNA-RNA-3' primer; (2) the products of primer extension are tailed at the 3' ends; (3) the desired products are amplified by PCR with oligonucleotides containing Illumina® adaptor sequences complementary to both tails and subjected to next-generation sequencing (NGS); 4) finally, positions of SSBs are revealed through the analysis of sequencing results.

10 Claims, 5 Drawing Sheets

Specification includes a Sequence Listing.

(56) References Cited

OTHER PUBLICATIONS

"Elongation of Displacement-Loop Strands in Human and Mouse Mitochondrial DNA is Arrested Near Specific Temple Sequences"; Oct. 1981; Jackie N. Doda, Catharine T. Wright and Davis A. Clayton; Proceedings of the National Academy of Sciences of the United States of America; vol. 78, No. 10, pp. 6116-6120.

"Regulation of DNA Replication at the End of the Mitochondrial D-Loop Involves the Hellcase Twinkle and a Conserved Sequence Element"; Aug. 2015; Elisabeth Jemt, Orjan Persson, Yonghong Shi, Majda Mehmedovic, Jay P. Uhler, Marvela Davila Lopez, Christoph Freyer, Clases M. Gustafsso, Tore Smuelsson and Maris Falkenberg; Nucleic Acids Research, vol. 43, No. 19, 14 pgs.

"Staphylococcal Nuclease: Proposed Mechanism of Action of Action Based on Structure of Enzyme-Thymidine 3',5'-Bisphosphate-Calcium Ion complex at 1/5-A Resolution"; Jun. 1979; F. Albert Cotton, Esward E. Hazen, Jr. and Margaret J. Legg; Proceedings of the National Academy of Sciences of the United States of America; vol. 76, No. 6, pp. 2551-2555.

"Radiation Dose-Rate Effects, Endogenous DNA Damage, and Signaling Resonance"; Nov. 2016; Michael M. Vilenchik and Alfred G. Knudson; Proceedings of the National Academy of Sciences of the United States of America; vol. 103, No. 47, 6 pgs.

"Endogenous DNA Double-Strand Breaks: Production, Fidelity of Repair, and Induction of Cancer"; Oct. 2003; Michael M. Vilenchik and Alfred G. Knudson; Proceedings of the National Academy of Sciences of the United States of America; vol. 100, No. 22, 7 pgs.

"Numerical Analysis of Etoposide Induced DNA Breaks"; Jun. 2009; Aida Muslimovic, Susanne Nystrom, Yue Gao and Ola Hammersten; Institute of Biomedicine, Department of Clinical Chemistry and Transfusion Medicine. vol. 4, Issue 6, PLoS One, 10 pgs.

"High-Resolution Profiling of yH2AX Around DNA Double Strand Breaks in the Mammalian Genome"; Feb. 2010; Jacon S. Iacovoni, Pierre Caron, Imen Lassadi, Estelle Nicolas, Lauren Massip Didier Trouche and Gaelle Legube; The Embo Journal; The European Molecular Biology Organization, vol. 29 No. 8; 12 pgs.

"In Vivo Formaldehyde Cross-Linking: It is time for Black Box Analysis"; Mar. 2015; Alexey Gavrilov, Sergey V. Razin and Giacomo Cavalli; Briefings in Functional Genomics, vol. 14, No. 2, pp. 163-165.

"Genotoxicity of Formaldehyde: Molecular Basis of DNA Damage and Mutation"; Sep. 2014; Masanobu Kawanishi, Tomonari Matsuda and Takashi Yagi; Frontiers in Environmental Science, vol. 2, Article 36, 8 pgs.

"In D-Loop: 40 Years 9f Mitochondrial 75 DNA"; Aug. 2014; Thomas J. Necholls and Mechal Minczuk; Experimental Gerontology, vol. 58, 7 pgs.

Czene, Stefan, et al., "Detection of single-strand breaks and formamidopyrimidine-DNA glycosylase-sensitive sites in DNA of cultured human fibroblasts", Mutation Rsearch, 1995, vol. 336, pp. 235-242.

Liu, Misha, et al., "Sensitive electrochemical detection of DNA damage based on in situ double strand growth via hybridization chain reaction", Anal Bioanal Chem, Sep. 29, 2017, vol. 409, pp. 6821-6829.

Cao, Huifen, et al., "Novel approach reveals genomic landscapes of single-strand DNA breaks with nucleotide resolution in human cells", Nature Communications, Dec. 20, 2019, Issue 10, vol. 5799, pp. 1-14.

Yue, Bao, et al., "An Efficient Detecting System for Gene's Recombination Caused by DNA Double Strand Breaks Using Direct Repeated Report Gene of GUS", Technology Style, Jun. 2018, pp. 15-18, with English abstract.

Corresponding Chinese Patent Application No. 201910837092.1, First Office Action, dated May 10, 2022.

Corresponding Chinese Patent Application No. 201910837092.1, Notification to Grant Patent, dated Aug. 31, 2022.

* cited by examiner

METHOD FOR DETECTING SINGLE STRAND BREAKS IN DNA

RELATED APPLICATION

This application claims priority to Chinese Patent Application 201910837092.1, filed on Sep. 5, 2019, which is incorporated herein by reference.

REFERENCE TO AN ELECTRONIC SEQUENCE LISTING

The contents of the electronic sequence listing (SequenceListing2.txt; Size: 2,038 bytes; and Date of Creation: Nov. 2, 2020) is herein incorporated by reference.

FIELD OF THE DISCLOSURE

The present disclosure relates to the field of biotechnology. More particularly, the present disclosure relates to a method called SSiNGLe-ILM (single-strand break mapping at nucleotide genome level on Illumina® sequencing platform) that can map single strand breaks (SSBs) in deoxyribonucleic acid (DNA) in a genome-wide range with nucleotide-level resolution using Illumina® next-generation sequencing platform.

BACKGROUND OF THE DISCLOSURE

DNA damage is now widely recognized as a major reason behind cancer and many other aging-associated diseases and as such represents a very important issue for human health. While multiple types of DNA lesions exist, SSBs are considered the most common type of DNA damage. These lesions can represent sites of oxygen radical DNA damage, intermediates in excision DNA repair pathway and products of unresolved intermediates of enzymes such as topoisomerases. SSBs can further deteriorate into highly toxic double-strand breaks (DSBs) by stalling or collapsing replication fork. However, by themselves, SSBs can also represent a major issue for cells as they can inhibit progression of ribonucleic acid (RNA) polymerase and in some cases cause apoptosis. The importance of this type of lesion is underscored by the existence of dedicated cellular pathways that deal with every step of fixing SSBs from detection to processing to repair. Defects in these pathways can lead to cellular sensitivity to genotoxic stress, embryonic lethality and a number of neurodegenerative diseases.

The remarkable progress in appreciation of the fine details of the SSB repair machinery however stands in stark contrast with the total absence of methods to map endogenous SSBs in a global, unbiased, and genome-wide range with nucleotide precision. This gap in available methodologies also contrasts with a suite of comprehensive approaches developed for mapping DSBs with nucleotide-level resolution, such as BLESS (breaks labeling, enrichment on streptavidin and next-generation sequencing), BLISS (Breaks Labeling In Situ and Sequencing) and others. Only one SSB genome-wide mapping method is believed to provide comprehensive and unbiased data. The procedure relies on the 3'OH group of an SSB to prime a DNA polymerase I nick-translation reaction that labels downstream DNA with a biotinylated nucleotide. The labeled DNA is then purified and subjected to next-generation sequencing. However, this approach maps a region of DNA, quite possibly extending thousands of bases from the original SSB, thus precluding identification of the lesion with nucleotide precision. On the other hand, a nucleotide-level method to map sites of excision repair has been developed; however, it cannot provide information on breaks generated by other mechanisms.

Thus, all this leads to a total dearth of knowledge of nucleotide-level genome-wide patterns for this critical type of DNA lesion. Here, an approach, SSiNGLe-ILM, is developed and validated that can provide nucleotide level maps of native SSBs genome-wide. This approach is implemented to work with the commonly used Illumine platform. The results show that the genomic pattern of breaks—the SSB "breakome"—has strong potential to represent a novel dimension describing state of a biological system and a novel source of blood-based biomarkers.

BRIEF SUMMARY OF THE DISCLOSURE

The present disclosure provides a method called SSiNGLe-ILM (single strand breaks in DNA mapping at nucleotide-level on Illumina® sequencing platform. The method can map single strand breaks (SSBs) in DNA in a genome-wide range of with nucleotide-level resolution using Illumina® next generation sequencing platform.

In order to solve the aforementioned technical problems, a technical solution adopted by the present disclosure is as follows.

A method for detecting single strand breaks (SSBs) in DNA comprising: 1) fragmenting DNA to be tested with a method that generates 3' ends that cannot be tailed to generate fragmented DNA; 2) adding a first tail to available 3' ends of SSBs of the fragmented DNA corresponding to tag endogenous breaks to generate tailed fragments; 3) capturing and identifying positions of SSBs genome-wide; and 4) revealing positions of the SSBs through an analysis of sequencing results. The capturing and identifying comprises processing samples of the tailed fragments as follows: linearly amplifying the tailed fragments using cycles of primer extension with a chimeric 5'-DNA-RNA-3' primer; adding a second tail to 3' ends of the products of the primer extension to obtain desired products; and amplifying the desired products by a polymerase chain reaction (PCR) with oligonucleotides comprising adaptor sequences complementary to both the first tail and the second tail and subjecting to next generation sequencing (NGS) to generate the sequencing results.

In a preferred embodiment, the fragmenting comprises fragmenting the DNA to be tested with a micrococcal nuclease (MNase) that generates 3'-phosphate ends. Conceivably, other fragmentation methods besides MNase can be used provided that the 3' ends generated during fragmentation cannot be tailed.

In a preferred embodiment, the fragmented DNA has a range of 150 to 500 base pairs. However, the range can be adjusted to suit other next generation (e.g., $2^{nd}$ or higher generation) sequencing platforms.

In a preferred embodiment, bases of the first tail and bases of the second tail can be different bases provided that the bases of the first tail and the bases of the second tail are not complementary. For example, if the bases of the first tail are polyA, the bases of the second tail should be polyC, polyG, or other bases, while polyT or polyU cannot be used. If dATP is used in the first tail, its optimal length range is 50-500 bases. However, a longer length range of dATP is also applicable.

In a preferred embodiment, the chimeric 5'-DNA-RNA-3' primer has a variable DNA base length provided that the chimeric 5'-DNA-RNA-3' primer is annealed to the first tail applied under the reaction conditions employed. In a preferred embodiment, 50 DNA bases are used. The RNA base region is variable in length provided that the RNA base region cannot be tailed by a terminal transferase (TdT) and can be converted into DNA by the PCR during DNA copying initiated from the second tail.

In a preferred embodiment, a length of bases of the second tail is variable. If dCTP is used in the second tail, an optimal length of the dCTP is 10 to 100 bases. A longer length range of dCTP is also applicable.

For the first tail and the second tail, polyA, polyG, polyC, or polyT is selected according to the principle described above.

In a preferred embodiment, while amplifying the desired products corresponding to SSBs, a primer pair is required to contain first sequences complementary to the first tail and the second tail and second sequences required for the NGS. In a preferred embodiment, the first sequences are 12T and 10G. However, the first sequences length and bases are variable provided that they can be annealed to the first tail and the second tail. The second sequences are also variable, but should match the requirements of the specific NGS platform used. In a preferred embodiment, primer sequences are sequences applicable to the Illumine' sequencing platform. In some embodiments, DNA breaks are in a first read, or in a second read of a read pair or in a single read.

In a preferred embodiment, revealing the positions of the SSBs comprises: selecting paired-end raw reads, where a first read starts with a corresponding number of complementary bases of the second tail and a second read starts with a corresponding number of complementary bases of the first tail. Depending on a design of primers, the first read and the second read may start with the bases complementary to the first tail and second tail, however, both the first read and the second read should have an expected number of bases complementary to the bases in the first tail and the second tail. The selected paired-end raw reads are then aligned to assemblies of specified genomes. Preferably, only pairs of reads where the first read and the second read uniquely mapped to a genome of the specified genomes with preset configuration and spacing are kept. However, depending on specific analysis needs, non-uniquely mapping reads can also be used. Reads generated in a product of the PCR due to matching to the endogenous DNA sequence similar to the first tail are removed. Here, if a fraction of T's in a 20-base 5' upstream sequence in a second read alignment is >40%, then such read-pair is removed from downstream analyses. An SSB is defined as a first base after a primer of a right number of the second read in the second read. By way of example, an SSB is defined as a first base after 12 T's in the second read. However, if a PCR primer contains sequences with more than 12 T's or other sequences, the analysis can be adjusted accordingly. Breaks found in the un-tailed samples are removed.

The disclosure also provides an application of this method for double-strand DNA break detection.

Compared to existing techniques, the technical solution of the present disclosure has the following advantages.

This is the only available method to identify all SSBs in a genome with nucleotide precision for Illumina® platform. It has the following properties.

This method can detect SSBs produced by various mechanisms with nucleotide precision.

The method can be easily applied to other NGS platforms, for example Ion Torrent and others, by changing the sequences of the primers during PCR.

The method can detect breaks with 3'-OH ends as well as other ends as shown by detection of 3'-P ends (where P is —PO4 phosphate group) after conversion into 3'-OH ends by treatments with SAP.

The method can be applied to test SSBs produced under a variety of environmental, disease or developmental conditions.

The method can be applied to cell lines or tissues.

The method can be applied to different species and types of DNA—nuclear genomes, organelle genomes, environmental samples and circulating DNA.

The method can also be applied to map double-strand breaks.

BRIEF DESCRIPTION OF THE DRAWINGS

The present disclosure will be further described below with reference to the drawings and embodiments.

FIG. 1 illustrates a flow chart of a method of SSiNGLe-ILM. DNA with 3'-OH SSB (hollow circles) is fragmented in situ with MNase that leaves 3'-P termini (solid circles) unable to be tagged with the polyA using TdT. After being tailed, the native DNA is further processed as shown and subjected to Illumine sequencing.

FIGS. 2A-2G illustrates a validation of the method of SSiNGLe-ILM. More particularly.

DETAILED DESCRIPTION OF THE EMBODIMENTS

Procedures

Figure 1:
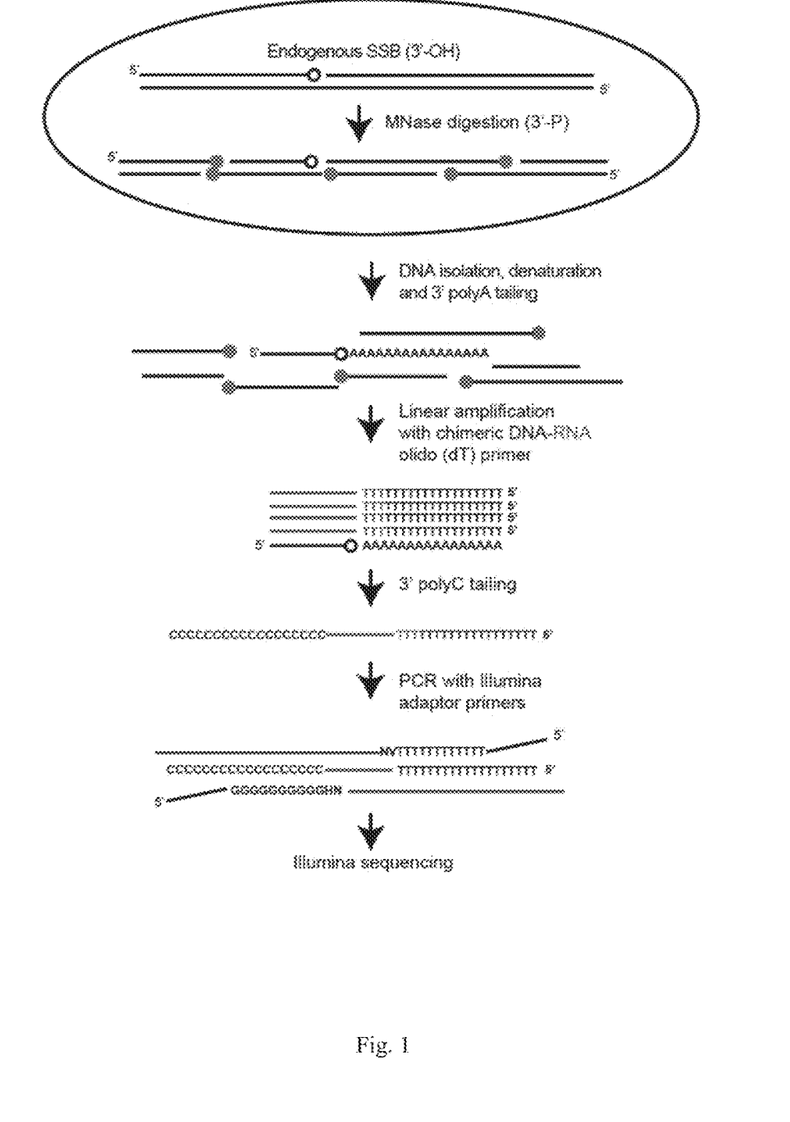

The essence of the present disclosure is based on tagging a free 3'-OH terminus representing an SSB by addition of a polyA-tail using terminal transferase (TdT) (FIG. 1).

Prior to the tagging, high-molecular weight (HMW) DNA is fragmented with micrococcal nuclease (MNase) that leaves 3'-phosphate ends that cannot be used as substrates for tailing by TdT and thus are not detectable by a subsequent method of the present disclosure (FIG. 1). This step avoids generating breaks via mechanical shearing of HMW DNA during subsequent purification and reduces the size of the HMW DNA to a range suitable for downstream NGS analyses.

Figure 2A:
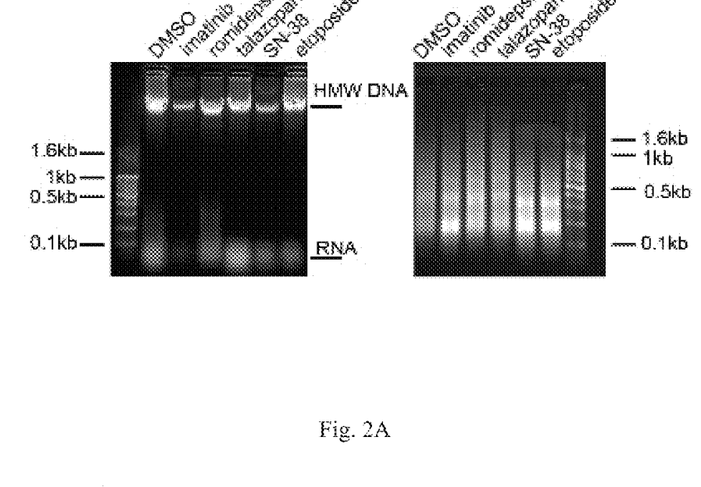
FIG. 2A illustrates agarose gel electrophoresis analysis results of genomic DNA isolated from cells treated for 48 hours with indicated drugs and then digested (right element of FIG. 2A) or not digested (left element of FIG. 2A) with MNase. A signal at a bottom of the agarose gel with un-digested material represents residual degraded RNA.

Prior to fragmentation, cells are cross-linked in situ with formaldehyde. Nuclei isolated from the crosslinked cells are then treated with MNase to fragment genomic DNA to a range of 150-500 base pairs (FIG. 2A). Following MNase inactivation, the nuclei are subjected to proteinase K treatment and cross-link reversal. The fragmented genomic DNA is then isolated, denatured and polyA-tailed with TdT to obtain polyA tags. The polyA tags then are used to capture and identify the positions of SSBs genome-wide using Illumina® sequencing (i.e., NGS) (FIG. 1) using the following 3 additional steps. First, the polyA-tailed molecules are linearly amplified using 10 cycles of primer extension with a chimeric DNA-RNA oligo-d(T)$_{50}$-r(T) 3 oligonucleotide consisting of 50 2'-deoxythymidine and 3 thymidine nucleotides at the 3' end to obtain products of primer extension. The last 3 RNA residues were included to prevent tailing of the oligonucleotide with TdT at the next step since the enzyme is unable to use RNA as a substrate of TdT. Second, the products of primer extension were tailed at the 3' end with polyC tail using TdT. Finally, desired molecules containing oligo-d(T)$_{50}$-r(T)$_3$ sequences at the 5' ends and polyC-tail at the 3' ends were exponentially PCR amplified with oligonucleotides containing Illumina® adaptor sequences (FIG. 1) and subjected to Illumina® sequencing (i.e., NGS).

Technical Details

Preparation of nuclei prior to MNase fragmentation: 1-6 million cells were crosslinked in 2 mL of either a growth medium (Human erythroleukemia cells (K562)) or phosphate-buffered saline (PBS) (peripheral-blood mononuclear cells (PBMCs)) supplemented with 1% formaldehyde for 10 minutes at room temperature (e.g., 20-25° C.) followed by addition of glycine (Thermo Fisher Scientific) to a final concentration of 1.375 M (Mol/L) to quench crosslinking for 5 minutes at room temperature. The cells were collected by centrifugation at 1500 g at 4° C., and then washed with ice-cold 1X PBS. To prepare nuclei, the cross-linked cells were lysed in a buffer containing 5 mM piperazine-N,N'-bis(2-ethanesulfonic acid (PIPES) (pH8), 3 mM Potassium chloride (KCl), 0.5% NP-40 (Amresco) for 10 minutes on ice, followed by centrifugation at 1000 g for 10 minutes at 4° C. After removal of supernatant, the nuclei were resuspended in 500 μL ice-cold 1X MNase buffer (NEB) and sedimented again under the same centrifugation conditions.

SDS permeabilization: relatively small MNase (17 kDa) can diffuse into nuclei via nuclear pores. However, treatment of DNA with larger enzymes, for example restrictases (restriction enzymes) or shrimp alkaline phosphatase (SAP), requires permeabilization with SDS. After removal of supernatant, the nuclei were resuspended in 100 μL ice-cold 1X MNase buffer per 1 million nuclei and split into aliquots of 1 million. Each aliquot was incubated with 0.3 Volume % of sodium dodecyl sulfate (SDS) for 1 hour at 37° C. with gentle mixing. Then, triton X-100 was added to concentration of 1.8 Volume % and incubated for 5 minutes at room temperature. If to be used directly for the MNase treatment, the nuclei were collected by centrifugation at 3500 g at 27° C. for 10 minutes and then washed twice with 1X MNase buffer. If subjected to the restriction enzyme digestion, then processed as below. Since K562 nuclei were used in restriction enzyme digestion experiments to validate SSiNGLe-ILM, all K562 and other cell line samples (HeLa and N2a) were processed with the SDS permeabilization step in the SSiNGLe-ILM protocol. However, PBMCs were processed without it (i.e., all samples tested with the SSiNGLe-SMS protocol were processed without the SDS permeabilization step).

Restriction enzyme digestion inside nuclei: the permeabilized nuclei were collected by centrifugation at 3500 g at 27° C. for 10 minutes and then washed twice with a 1× NEB buffer 2.1 (50 mM NaCl, 10 mM Tris-HCl, and 10 mM MgCl$_2$). After removal of supernatant, the nuclei were resuspended in 50 μL of 1X NEB buffer 2.1 and treated (digested) with 50 U of restriction enzymes Nt.BbvCI with or without 1U of SAP (NEB) for 2 hours at 37° C., and then treated for 20 minutes at 70° C. to inactivate the enzymes. The nuclei were collected by centrifugation at 3500 g at 27° C. for 10 minutes and then washed twice with 1X MNase buffer.

MNase fragmentation and DNA purification: after removal of supernatant, the nuclei were resuspended in 50 μL of cold 1X MNase buffer with 100 μg/mL bovine serum albumin (BSA) per 1 million nuclei and split into aliquots of 1 million. Each aliquot was digested separately with 1200-3000 units of MNase (NEB) and 200 units of RNAIf (NEB) for 30 minutes on ice. The digestion products were checked on 1% agarose gel after DNA purification to ensure that the majority of DNA was in the range of 150-500 bp as exemplified in FIG. 2A. After MNase digestion, 5.6 μL of 0.5 M ethylenediaminetetraacetic acid (EDTA) and 150 μL of nuclei lysis buffer (10 mM EDTA, 1% SDS, 10 mM Tris-HCl pH 8) was added to the mix. After 5 minutes of incubation at room temperature, 1 μL of 20 μg/mL proteinase K (Roche) was added followed by incubation for 45 minutes at 55° C. and 45 minutes at 65° C. The DNA was then precipitated with 0.3 M KCl and ice-cold isopropanol for 30 minutes at −80° C., followed by 15-minute centrifugation at 4° C. at 12,000 g, washing with ice-cold 70% ethanol and vacuum-drying. The DNA pellet was then dissolved in 40 μL water followed by purification with 2×volumes of VAHTS DNA Clean Beads (Vazyme). The concentration of DNA was measured using Qubit 3.0 fluorometer and "dsDNA HS Assay" kit (Thermo Fisher Scientific). In parallel, for every sample, DNA was isolated using the same procedure but without the MNase treatment step to ensure that the original DNA was present in HMW form as exemplified in FIG. 2A.

Tagging of breaks using polyA-tailing with TdT: 100 ng of the purified fragmented DNA was denatured at 95° C. for 5 minutes in 19 μL volume containing 2 μL of 10× TdT buffer, 2 μL of 2.5 mM CoCl$_2$ and water followed by rapid snap-cooling on ice. TdT (4 units; NEB) and 2 μL of 1 mM (SSiNGLe-SMS profiling of K562 cells) or 10 mM (all other experiments, SSiNGLe-SMS or SSiNGLe-ILM) dATP were then added to denatured DNA to the total volume of 22 μL and incubated at 37° C. for 30 minutes. To block free 3'-OH ends, 2 μL of 1 mM (SSiNGLe-SMS profiling of K562 cells) or 10 mM (all other experiments, SSiNGLe-SMS or SSiNGLe-ILM) ddNTP (either one of ddCTP, ddGTP, ddATP or ddTTP) was added to the tailing mix and incubated at 37° C. for additional 30 minutes, followed by incubation at 70° C. for 10 minutes to inactivate TdT and either used directly for SMS or processed further for SSiNGLe-ILM.

Linear amplification: the tailing mix was purified with 2×volumes of VAHTS beads, eluted in 16.2 μL water, and used entirely for the linear amplification of the polyA-tailed molecules as follows. The eluted DNA was mixed with 2 μL of PCR buffer, 0.4 μL of 10 mM dNTP mix (Invitrogen), 1 μL of 10 μM of a chimeric DNA-RNA oligo-d(T)$_{50}$-r(T)$_3$ oligonucleotide (50 2'-deoxythymidine and 3 thymidine nucleotides at the 3' end) and 1U of Taq DNA polymerase (Tiangen). The amplification conditions were as follows: initial denaturation at 94° C. for 30 seconds, followed by 10 cycles of denaturation at 94° C. for 1 minute, annealing at 55° C. for 30 seconds and extension at 72° C. for 30 seconds. After this, the DNA was purified with 2×volumes of VAHTS beads and eluted in 15 μL of water.

polyC tailing: the eluted DNA was denatured at 95° C. for 5 minutes in 19 μL volume with 2 μL of 10×TdT buffer and 2 μL of 2.5 mM CoCl$_2$ followed by rapid snap-cooling on ice. Four units of TdT (NEB) and 2 μL of 10 mM dCTP (Roche) were then added to denatured DNA to the total volume of 22 μL and incubated at 37° C. for 30 minutes. To block free 3'-OH ends, 2 μL of 10 mM ddCTP (Roche) was added to the tailing mix and incubated at 37° C. for additional 30 minutes, followed by incubation at 70° C. for 10 minutes to inactivate TdT.

Library construction—PCR condition 1: the polyC-tailed DNA was purified with 2× volume of VAHTS beads, eluted in 15.2 μL water, and used in its entirety for the library construction as follows. The eluted DNA was subjected to PCR amplification in 20 μL reaction volume containing: 1× PCR buffer, 0.4 μl of 10 mM dNTP mix (Invitrogen), 1 μL of each of the following two oligonucleotides Illumina®_P5G10 (SEQ ID No: 1) (AATGATACGGCGACCACCGAGATCTACACTCTTTCCCTACACGACGCTCTT CCGATCTGGGGGGGGGGHN) and Illumina®_P7T12 (SEQ ID No: 2) (CAAGCAGAAGACGGCATACGAGATCGTGATGTGACTGGAGTTCAGACGTG TGCTCTTCCGATCTTTTTTTTTTTTVN) each at 10 μM and 1U of Taq DNA polymerase (Tiangen). The PCR conditions were as follows: (1) initial denaturation at 94° C. for 3 minutes; (2) followed by 1 cycle of denaturation at 94° C. for 30 seconds, annealing at 55° C. for 1 minute and extension at 72° C. for 1 minute; (3) denaturation at 94° C. for 30 seconds, annealing at 37° C. for 1 minute and slow ramp at 2° C. per minute to 72° C. followed by 2 minutes incubation, followed by (4) 30 cycles of incubation at 94° C. for 30 seconds and extension at 72° C. for 1 minute. The amplified DNA was purified with 2× volumes of VAHTS beads and eluted in 20 μL of water. The concentration of DNA was measured using Qubit 3.0 fluorometer and "dsDNA HS Assay" kit (Thermo Fisher Scientific). Sequencing on the Illumina® platform was performed using paired-end 150 bp strategy and outsourced to Novogene Corporation (Beijing). Library construction—PCR condition 2: Alternatively, to increase the yield, the following approach based on 2 rounds of PCR amplification can be used. The polyC-tailed DNA was purified with 2× volume of VAHTS beads, eluted in 15.2 μL water, and used in its entirety for the library construction as follows. The eluted DNA was subjected to PCR amplification in 20 μL reaction volume containing 1× PCR buffer, 0.4 μL of 10 mM dNTP mix (Invitrogen), 1 μL of each of the following two oligonucleotides P5G10 (SEQ ID No: 3) (CTACACGACGCTCTTCCGATCTGGGGGGGGGGHN) and P7T12 (SEQ ID No: 4) (GTTCAGACGTGTGCTCTTCCGATCTTTTTTTTTTTTVN) each at 10 μM and 1U of Taq DNA polymerase (Tiangen). The PCR conditions were as follows: (1) initial denaturation at 94° C. for 3 minutes; (2) followed by 1 cycle of denaturation at 94° C. for 30 seconds, annealing at 55° C. for 1 minute and extension at 72° C. for 1 minute; (3) 1 cycle of denaturation at 94° C. for 30 seconds, annealing at 37° C. for 1 minute and slow ramp at 2° C. per minute to 72° C. followed by 2 minutes incubation; (4) 10-30 cycles of incubation at 94° C. for 30 seconds, annealing at 60° C. for 30 seconds and extension at 72° C. for 30 seconds followed by (5) incubation for 7 minutes at 72° C. Note: if the products are to be sequenced on the Illumina® NovaSeq platform, the P5_G10 oligonucleotide has to be substituted for P5_N10G10 (SEQ ID No: 7) (CTACACGACGCTCTTCCGATCTAGTTGCGGATGGGGGGGGGGHN) in the PCR reaction above.

The reaction was purified with 2× volume of VAHTS beads and eluted in 15 μL water. A fraction (25-100%) of the reaction was used for the next round of PCR amplification in 20 μL reaction volume containing: 1x PCR buffer, 0.4 μL of 10 mM dNTP mix (Invitrogen), 1 μL of each of the following two oligonucleotides Illumina®_P5 (SEQ ID No: 5) (AATGATACGGCGACCACCGAGATCTACACTCTTTCCCTACACGACGCTCTT CCGATCT) and Illumina®_P7 (SEQ ID No: 6) (CAAGCAGAAGACGGCATACGAGATCGTGATGTGACTGGAGTTCAGACGTG TGCTCTTCCGATCT) each at 10 μM and 1U of Taq DNA polymerase (Tiangen). The PCR conditions were as follows: (1) initial denaturation at 94° C. for 3 minutes; (2) cycles of denaturation at 94° C. for 30 seconds, annealing at 55° C. for 30 seconds and extension at 72° C. for 30 seconds followed by (3) incubation for 7 minutes at 72° C. The amplified DNA was purified with 2× volumes of VAHTS beads and eluted in 20 μL of water. The concentration of DNA was measured using Qubit 3.0 fluorometer and "dsDNA HS Assay" kit (Thermo Fisher Scientific). Sequencing on the Illumina® platform was performed using paired-end 150 bp strategy and outsourced to Novogene Corporation (Beijing).

Processing of Raw Illumina® Reads and Mapping SSBs (1) Only paired-end raw reads where read 1 started with 10 G's, read 2 started with 12 T's and each base of each read having a Phred quality score >20 was selected.

(2) Such reads were then aligned to the GRCh37/hg19 or GRCm38/mm10 assemblies of human or mouse genomes respectively using BWA-MEM (Version with default settings. For the detection of the 7S DNA species (FIGS. 2F & 2G) reads were mapped only to the chrM sequence. Only pairs of reads where both reads 1 and 2 uniquely mapped to the genome with appropriate configuration and spacing were kept.

(3) Pairs of reads where a fraction of T's in the 20-base 5' upstream sequence in the read 2 alignment was >40% were removed from the downstream analyses. An SSB was defined as the first base after 12 T's in the read 2. Breaks found in the un-tailed samples were removed.

Validation of the Method

Figure 2B:
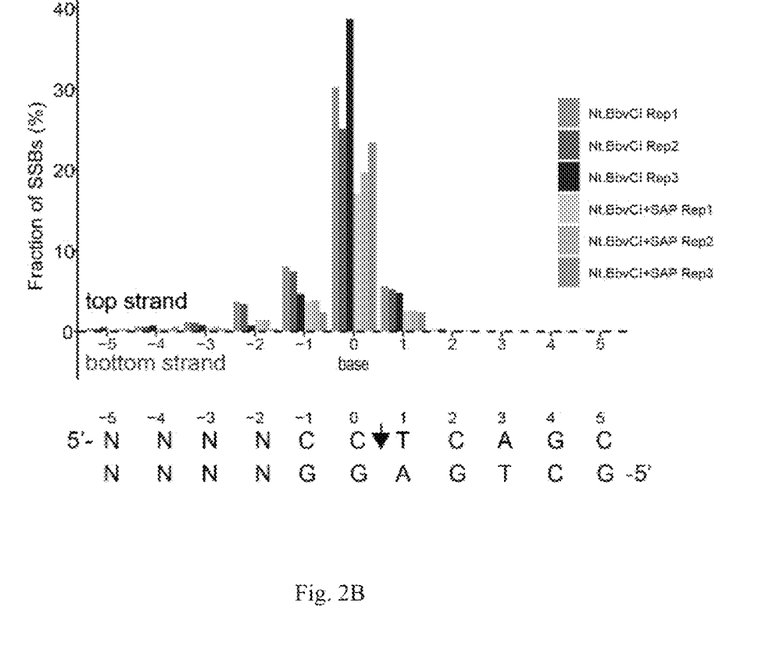
FIG. 2B illustrates results of three replicas ("Rep 1"-"Rep 3") of in situ digestion of nuclei from $H_2O_2$-treated K562 cells using Nt.BbvCI with or without SAP. A fraction of SSBs found by SSiNGLe-ILM mapping to each of the indicated bases of the Nt.BbvCI sites is represented by the y-axis and flanking sequences for the top and bottom strands of the site are represented by the x-axis. The cleavage site is shown with the arrow.

First, whether SSBs could be indeed detected by using a nicking site-specific restriction endonuclease Nt.BbvCI that can digest only the top strand of CCTCAGC site was tested. Cross-linked nuclei were digested with Nt.BbvCI prior to MNase fragmentation. Indeed, as shown in FIG. 2B, a very high enrichment (152 fold) of breaks mapping to the correct strand of the CCTCAGC site were observed. Second, digestion with this enzyme allowed testing to determine whether the method indeed has nucleotide-level precision. In fact, a majority (25-35%) of Nt.BbvCI-induced breaks mapped to the correct base, and the vast majority (38-42%) were within 1 base of the predicted cut site (FIG. 2B). Third, whether breaks with termini other than 3'-OH could be detected were tested. To accomplish this, nuclei with Nt.BbvCI in the presence shrimp alkaline phosphatase (SAP) that converts 3'-phosphates to 3'-OH termini were digested. The former termini commonly occur in response to some DNA damaging agents, such hydrogen peroxide treatments, therefore these experiments were done on nuclei of cells treated with $H_2O_2$. Since Nt.BbvCI produces 3'-OH termini, the treatment with SAP would not affect detection of these sites. However, if as expected, additional breaks became detectable after this treatment, then the fraction of Nt.BbvCI reads would decrease in the SAP treated vs un-treated cells, and this is exactly what was observed in multiple independent replicas as shown in FIG. 2B.

Figure 2C:
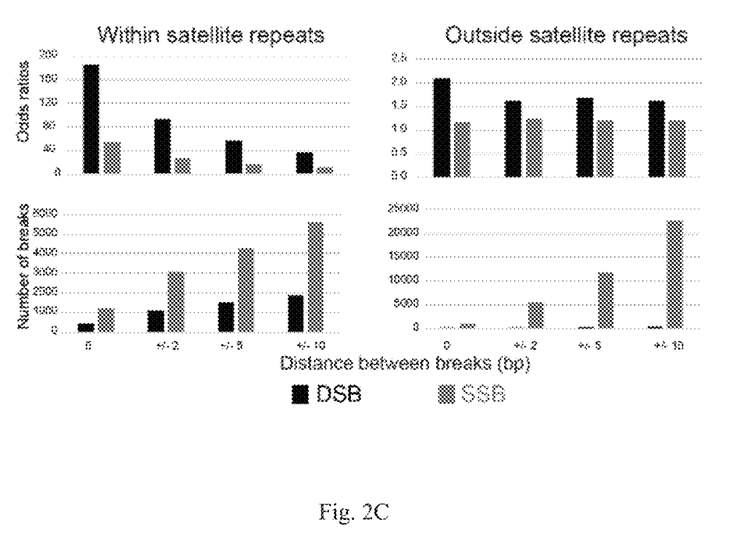
FIG. 2C illustrates overlap between SSBs or DSB found by SSiNGLe-ILM in HeLa cells with DSBs found by BLESS protocol. The odds ratios and numbers of overlapping breaks are shown for the different distances between the breaks in the two datasets.

Second, theoretically, both SSBs and DSBs should be captured by this approach, however since the former outnumber the latter by 2-3 orders of magnitude, even after treatments with such well-known DSB-inducing drugs as etoposide, the predominant signal is expected to derive from SSBs. Still, the ability of the disclosed SSiNGLe-ILM method to detect endogenous DSBs was tested by two approaches. First, detection of exogenous DSBs caused by a well-characterized rare-cutting restriction endonuclease AsiSI represented by 2,484 sites in the human genome was tested. Unlike Nt.BbvCI, however, DNA cleavage at the AsiSI sites were not detected after treating cross-linked nuclei with this enzyme using either real-time PCR on selected sites or the disclosed genome-wide approach (data not shown). Therefore, purified DNA after the MNase fragmentation with AsiSI was digested before tailing and then subjected the purified DNA to the SSiNGLe-ILM procedure. Indeed, breaks on both strands of the expected target sites were detected, a majority (51.6%) of which mapped to the correct base and most (84.4%) within 1 base of the expected cleavage site. Second, detection of endogenous DSBs was tested by comparing SSiNGLe-ILM profiles of breaks in HeLa cells and those obtained using BLESS protocol. DSBs were defined as two SSBs occurring on opposite strands in the SSiNGLe-ILM data. Indeed, a statistically-significant overlap between the two datasets was observed, with a very strong reproducible enrichment in satellite repeats (odds ratios 208-343 of enrichment relative to expected by random chance) (FIG. 2C). The enrichment was highest with the exact match of genomic coordinates and decreased with increasing the overlap between the breaks in the two datasets (FIG. 2C). The overlap was significantly lower, but still statistically-significant in the regions outside of the satellite repeats (FIG. 2C).

Figure 2D:
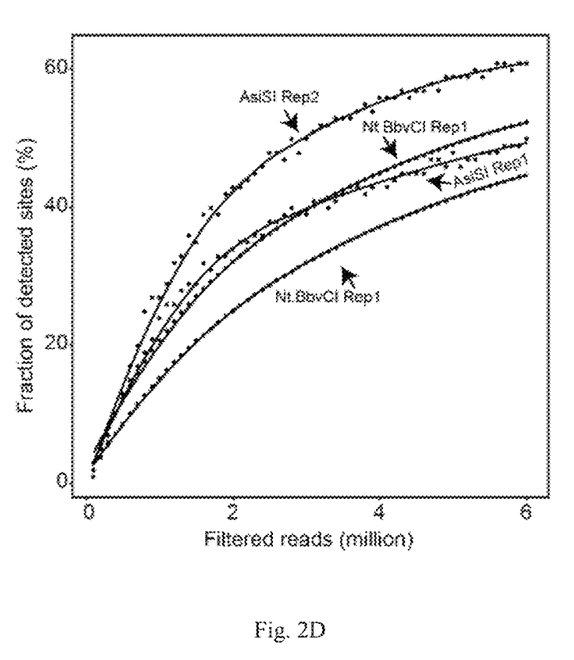
FIG. 2D illustrates a fraction of detected AsiSI and Nt.BbvCI sites (Y-axis) at different numbers of filtered reads (X-axis). Each experiment was done in two replicas.

Third, the sensitivity of detection of SSBs and DSBs was investigated using SSiNGLe-ILM. Deep sequencing of the above mentioned samples digested with AsiSI and Nt.BbvCI revealed that 2.8M uniquely-aligned and filtered reads can be sufficient to detect 50% of the 1242 AsiSI sites in the human genome (FIG. 2D). This number increases to 5.1M such reads required for detection of 50% of the 1.4M Nt.BbvCI sites (FIG. 2D). Overall, approximately 50M and 18M filtered reads were estimated to be required to detect close to 100% of the AsiSI and Nt.BbvCI sites.

SSiNGLe-ILM was then applied to profile breaks occurring in human leukemia K562 cells treated with 7 anti-cancer medications—etoposide (inhibitor of Topoisomerase II), SN-38 (inhibitor of Topoisomerase I), romidepsin (inhibitor of histone deacetylases), imatinib (inhibitor of BCR-ABL oncogene present in K562), talazoparib (PARP inhibitor), 10074-G5 (c-Myc inhibitor) and YM-155 (DNA intercalator) and dimethyl sulphoxide (DMSO) control for 6, 12, 24, 36 and 48 hours. After 36-48 hours, all of the treatments including DMSO caused marked increase in apoptotic cells as assessed by fluorescence-activated cell sorting (FACS) with Annexin V staining, while most of the DNA was still in HMW form as judged by the agarose gel (FIG. 2A).

Figure 2E:
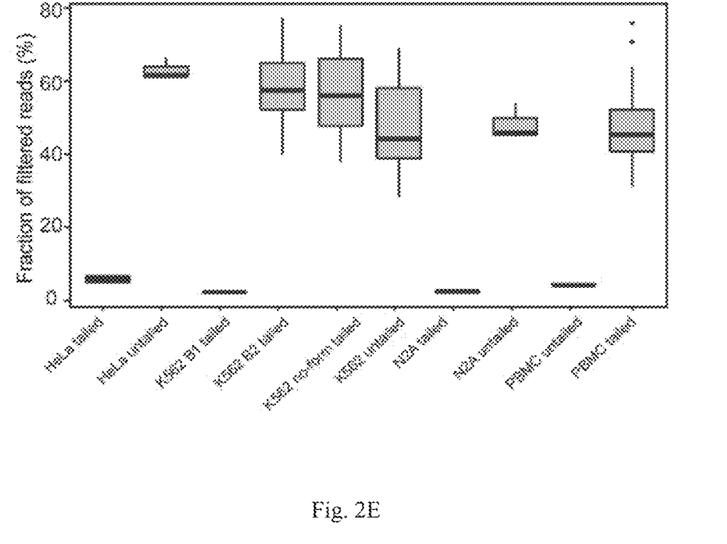
FIG. 2E illustrates fraction of uniquely aligned reads that survives filtration for the adjacent endogenous polyA stretches in different tailed and untailed samples.

Importantly, 44-86% (median 72%) of the Illumina® reads from the polyA-tailed samples could be uniquely mapped to the genome. Furthermore, 38-77% (median 57%) of those survived the filtration for proximity to internal polyA-stretches compared to only 2-3% in the corresponding un-tailed controls (FIG. 2E). Moreover, the fraction of post-filtered reads in tailed samples were fairly consistent between the two different biological replicas performed (FIG. 2E). This approach was further tested on human peripheral blood mononuclear cells (PBMCs), 3 biological replicas of human HeLa and mouse Neuro2A cell lines. As expected, a significantly higher fraction of filtered reads in the tailed samples was observed from these cell types compared with the un-tailed controls (2.2-4.2% filtered reads in the un-tailed vs 44.8-66.4-% in the tailed samples, median 57%) (FIG. 2E).

While broadly used in many methodologies, including DNA break mapping, formaldehyde crosslinking has been reported to cause artifacts and even DNA damage. To evaluate the potential effect of the crosslinking step per se to the breaks detected by SSiNGLe-ILM, a separate biological replica of K562 cells treated with etoposide, romidepsin and DMSO for 6, 12, 24, 36 and 48 hours was processed without the formaldehyde crosslinking step. In these samples, a similar fraction of reads surviving the filtration step as in the crosslinked samples were observed (FIG. 2B).

Figure 2F:
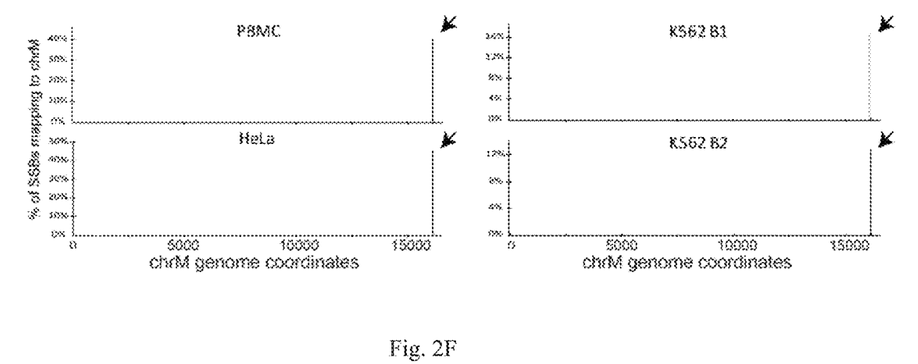
FIG. 2F illustrates a median fraction of SSBs (Y-axis) mapping to each base (X-axis) of the minus or H strand of the chrM genome, shown for each of the 3 sample types. The peaks of the signal are shown by arrows.
Figure 2G:
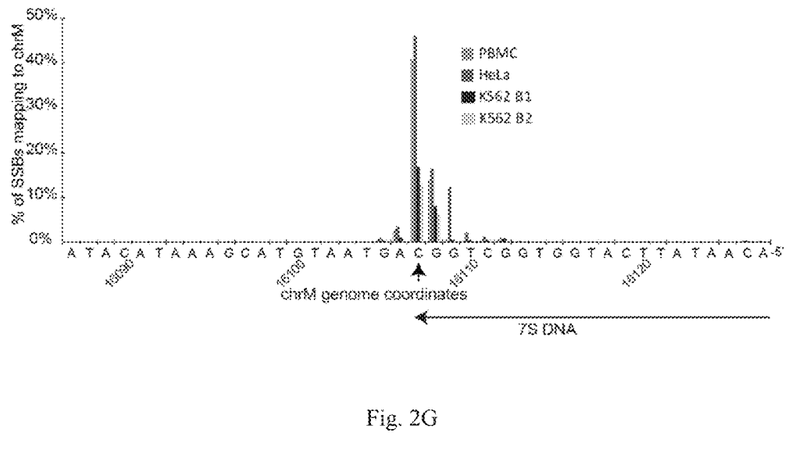
FIG. 2G illustrates a zoomed-in view on the region of the major peak in the panel shown by arrows in FIG. 2F. The arrow below the X-axis represents the previously-reported 3' end of 7S DNA. Only background-level signal can be observed on the opposite strand.

Finally, the ability of the disclosed method to detect endogenous SSBs was tested. To detect 7S DNA (FIGS. 2F and 2G), reads merely mapped to chrM. The mitochondrial 7S DNA is a naturally-occurring small single-strand DNA molecule with 3'OH terminus whose exact position has been previously established. Thus, the 3'OH terminus of this molecule can serve as a surrogate for a characterized naturally-occurring SSB. Since large numbers of reads mapped to the mitochondrial genome (chrM) in various types of samples (median number of chrM reads for a cell type in the range of 1,598-27,606), it would be expected that the disclosed approach should detect the 3' end of 7S DNA. Indeed, as shown in FIG. 2F, a clear peak of accumulation of SSBs on the expected (minus or H (heavy)) strand of the mitochondrial genome mapping to the location of the 3' end of the 7S DNA molecule in PBMC, HeLa and K562 samples was observed. Strikingly, the exact position of that peak coincided precisely with the position reported earlier in all 3 types of samples as shown in FIG. 2G. Furthermore, the signal was only found on the correct strand. The fraction of mitochondrial reads mapping to the 3' end of 7S DNA was reproducible as illustrated by the two biological replicas of K562 cells (FIG. 2G). However, the fraction also varied among the 3 sample types, likely reflecting reported differences in abundances of the 7S DNA among different cell types (FIG. 2G). Overall, these results show that the disclosed method can consistently and accurately detect endogenous SSBs among different cell types and different species with nucleotide-level resolution.

Embodiment 2

Embodiment differs from Embodiment as follows.

Preparation of nuclei prior to MNase fragmentation: 1-6 million cells were crosslinked in 2 mL of either a growth medium (Human erythroleukemia cells (K562)) or phosphate-buffered saline (PBS) (peripheral-blood mononuclear cells (PBMCs)) supplemented with 1% formaldehyde for 10 minutes at room temperature (e.g., followed by addition of glycine (Thermo Fisher Scientific) to a final concentration of 0.125 M (Mol/L) to quench crosslinking for 5 minutes at room temperature. The cells were collected by centrifugation at 220 g at 4° C., and then washed with ice-cold 1X PBS. To prepare nuclei, the cross-linked cells were lysed in a buffer containing 5 mM piperazine-N,N'-bis(2-ethanesulfonic acid (PIPES) (pH8), mM Potassium chloride (KCl), 0.5% NP-40 (Amresco) for 10 minutes on ice, followed by centrifugation at 300 g for 10 minutes at 4° C. After removal of supernatant, the nuclei were resuspended in 500 μL ice-cold 1X MNase buffer (NEB) and sedimented again under the same centrifugation conditions.

SDS permeabilization: relatively small MNase (17 kDa) can diffuse into nuclei via nuclear pores. However, treatment of DNA with larger enzymes, for example restrictases (restriction enzymes) or shrimp alkaline phosphatase (SAP), requires permeabilization with SDS. After removal of supernatant, the nuclei were resuspended in 100 μL ice-cold 1X MNase buffer per 1 million nuclei and split into aliquots of 1 million. Each aliquot was incubated with 0.3 Volume % of sodium dodecyl sulfate (SDS) for 1 hour at 37° C. with gentle mixing. Then, triton X-100 was added to concentration of 1.8 Volume % and incubated for 5 minutes at room temperature. If to be used directly for the MNase treatment, the nuclei were collected by centrifugation at 1500 g at 27° C. for 15 minutes and then washed twice with 1X MNase buffer. If subjected to the restriction enzyme digestion, then processed as below. Since K562 nuclei were used in restriction enzyme digestion experiments to validate SSiNGLe-ILM, all K562 and other cell line samples (HeLa and N2a) were processed with the SDS permeabilization step in the SSiNGLe-ILM protocol. However, PBMCs were processed without it (i.e., all samples tested with the SSiNGLe-SMS protocol were processed without the SDS permeabilization step).

Restriction enzyme digestion inside nuclei: the permeabilized nuclei were collected by centrifugation at 1500 g at 27° C. for 10 minutes and then washed twice with a 1× NEB buffer 2.1 (50 mM NaCl, 10 mM Tris-HCl, and 10 mM MgCl$_2$). After removal of supernatant, the nuclei were resuspended in 50 μL of 1X NEB buffer 2.1 and treated (digested) with 50 U of restriction enzymes Nt.BbvCI with or without 1U of SAP (NEB) for 2 hours at 37° C., and then treated for 20 minutes at 70° C. to inactivate the enzymes. The nuclei were collected by centrifugation at 1500 g at 27° C. for 10 minutes and then washed twice with 1X MNase buffer.

MNase fragmentation and DNA purification: after removal of supernatant, the nuclei were resuspended in 50 μL of cold 1X MNase buffer with 200 μg/mL bovine serum albumin (BSA) per 1 million nuclei and split into aliquots of 1 million. Each aliquot was digested separately with 1200-3000 units of MNase (NEB) and 25 units of RNAIf (NEB) for 30 minutes on ice. The digestion products were checked on 1% agarose gel after DNA purification to ensure that the majority of DNA was in the range of 150-500 bp as exemplified in FIG. 2A. After MNase digestion, 5.6 μL of 0.5 M ethylenediaminetetraacetic acid (EDTA) and 150 μL of nuclei lysis buffer (10 mM EDTA, 1% SDS, 50 mM Tris-HCl pH 8) was added to the mix. After 5 minutes of incubation at room temperature, 1 μL of 20 mg/mL proteinase K (Invitrogen) was added followed by incubation for 45 minutes at 55° C. and 45 minutes at 65° C. The DNA was then precipitated with 0.15 M KCl and ice-cold isopropanol for 30 minutes at −80° C., followed by 15-minute centrifugation at 4° C. at 12,000 g, washing with ice-cold 70% ethanol and vacuum-drying. The DNA pellet was then dissolved in 40 μL water followed by purification with 2× volumes of VAHTS DNA Clean Beads (Vazyme). The concentration of DNA was measured using Qubit 3.0 fluorometer and "dsDNA HS Assay" kit (Thermo Fisher Scientific). In parallel, for every sample, DNA was isolated using the same procedure but without the MNase treatment step to ensure that the original DNA was present in HMW form as exemplified in FIG. 2A.

In the present disclosure, any numerical ranges include all values in the range.

It will be apparent to those skilled in the art that various modifications and variation can be made in the present disclosure without departing from the spirit or scope of the disclosure. Thus, it is intended that the present disclosure cover the modifications and variations of this disclosure provided they come within the scope of the appended claims and their equivalents.

What is claimed is:

1. A method for detecting single strand breaks (SSBs) in deoxyribonucleic acid (DNA) comprising:
   fragmenting DNA with the SSBs to obtain fragmented DNA with available 3' ends of the SSBs using a method that generates unavailable 3' ends that cannot be tailed to generate fragmented DNA;
   adding a first tail to the available 3' ends of the SSBs of the fragmented DNA to generate tailed fragments; and
   capturing and identifying positions of the SSBs genome-wide, wherein the capturing and identifying comprises:
      linearly amplifying the tailed fragments using cycles of primer extension with a chimeric 5'-DNA-RNA-3' primer;
      adding a second tail to 3' ends of products of the primer extension to obtain desired products;
      amplifying the desired products by a polymerase chain reaction (PCR) with oligonucleotides comprising adaptor sequences complementary to both the first tail and the second tail and subjecting to next-generation sequencing (NGS) to generate sequencing results; and
      revealing the positions of the SSBs through analysis of the sequencing results of the NGS.

2. The method for detecting SSBs in DNA of claim 1, wherein:
   the fragmenting comprises:
      fragmenting the DNA with a micrococcal nuclease (MNase) that generates 3'-phosphate ends.

3. The method for detecting SSBs in DNA of claim 1, wherein the fragmenting comprises fragmenting the DNA to a range of 150 to 500 base pairs.

4. The method for detecting SSBs in DNA of claim 1, wherein bases of the first tail and bases of the second tail are not complementary.

5. The method for detecting SSBs in DNA of claim 1, wherein the chimeric 5'-DNA-RNA-3' primer is annealed to the first tail.

6. The method for detecting SSBs in DNA of claim 1, wherein a length of dCTP used in tailing the second tail is 10 to 100 bases.

7. The method for detecting SSBs in DNA of claim 1, wherein the adaptor sequences are adaptor sequences applicable to second and higher generation sequencing systems.

8. The method for detecting SSBs in DNA of claim 1, wherein revealing the positions of the SSBs comprises:
   (1) selecting paired-end reads, where a first read starts with a corresponding number of complementary bases of the second tail and a second read starts with a corresponding number of complementary bases of the first tail,
   (2) aligning the paired-end reads after bases corresponding to PCR primers have been removed to assemblies of specified genomes, wherein only pairs of reads where the first read and the second read uniquely mapped to a genome of the specified genomes with preset configuration and spacing are kept, and
   (3) removing pairs of reads where a fraction of T's in a 20-base sequence of 5' upstream of an alignment of the second read of the paired-end reads is >40%, and defining an SSB as a first base in the second read of remaining read pairs of the paired-end reads.

9. The method for detecting SSBs in DNA of claim 1, wherein an SSB of the SSBs is present in a first read, or in a second read of a read pair or in a single read.

10. The method for detecting SSBs in DNA of claim 8, wherein defining the SSB comprises defining the SSB as the first base after 12 T's in the second read.

* * * * *

SEQUENCE LISTING

```
<160> NUMBER OF SEQ ID NOS: 7

<210> SEQ ID NO 1
<211> LENGTH: 70
<212> TYPE: DNA
<213> ORGANISM: Artificial Sequence
<220> FEATURE:
<223> OTHER INFORMATION: Synthesized
<220> FEATURE:
<221> NAME/KEY: Misc_feature
<222> LOCATION: 70
<223> OTHER INFORMATION: n represents an a or g or c or t/u in Table 1
      of Appendix 2 of WIPO Standard ST.25 (1998)

<400> SEQUENCE: 1
aatgatacgg cgaccaccga gatctacact ctttccctac acgacgctct tccgatctgg      60 ggggggggghn                                                           70

<210> SEQ ID NO 2
<211> LENGTH: 78
```

```
<212> TYPE: DNA
<213> ORGANISM: Artificial Sequence
<220> FEATURE:
<223> OTHER INFORMATION: Synthesized
<220> FEATURE:
<221> NAME/KEY: Misc_feature
<222> LOCATION: 78
<223> OTHER INFORMATION: n represents an a or g or c or t/u in Table 1
      of Appendix 2 of WIPO Standard ST.25 (1998)

<400> SEQUENCE: 2
caagcagaag acggcatacg agatcgtgat gtgactggag ttcagacgtg tgctcttccg      60 atctttttttt tttttttvn                                                 78

<210> SEQ ID NO 3
<211> LENGTH: 34
<212> TYPE: DNA
<213> ORGANISM: Artificial Sequence
<220> FEATURE:
<223> OTHER INFORMATION: Synthesized
<220> FEATURE:
<221> NAME/KEY: Misc_feature
<222> LOCATION: 34
<223> OTHER INFORMATION: n represents an a or g or c or t/u in Table 1
      of Appendix 2 of WIPO Standard ST.25 (1998)

<400> SEQUENCE: 3
ctacacgacg ctcttccgat ctggggggggg gghn                                34

<210> SEQ ID NO 4
<211> LENGTH: 39
<212> TYPE: DNA
<213> ORGANISM: Artificial Sequence
<220> FEATURE:
<223> OTHER INFORMATION: Synthesized
<220> FEATURE:
<221> NAME/KEY: Misc_feature
<222> LOCATION: 39
<223> OTHER INFORMATION: n represents an a or g or c or t/u in Table 1
      of Appendix 2 of WIPO Standard ST.25 (1998)

<400> SEQUENCE: 4
gttcagacgt gtgctcttcc gatctttttt tttttttvn                            39

<210> SEQ ID NO 5
<211> LENGTH: 58
<212> TYPE: DNA
<213> ORGANISM: Artificial Sequence
<220> FEATURE:
<223> OTHER INFORMATION: Synthesized

<400> SEQUENCE: 5
aatgatacgg cgaccaccga gatctacact ctttccctac acgacgctct tccgatct       58

<210> SEQ ID NO 6
<211> LENGTH: 64
<212> TYPE: DNA
<213> ORGANISM: Artificial Sequence
<220> FEATURE:
<223> OTHER INFORMATION: Synthesized

<400> SEQUENCE: 6
caagcagaag acggcatacg agatcgtgat gtgactggag ttcagacgtg tgctcttccg      60
atct                                                                  64

<210> SEQ ID NO 7
<211> LENGTH: 44
```

```
<212> TYPE: DNA
<213> ORGANISM: Artificial Sequence
<220> FEATURE:
<223> OTHER INFORMATION: Synthesized
<220> FEATURE:
<221> NAME/KEY: Misc_feature
<222> LOCATION: 44
<223> OTHER INFORMATION: n represents an a or g or c or t/u in Table 1
      of Appendix 2 of WIPO Standard ST.25 (1998)

<400> SEQUENCE: 7
ctacacgacg ctcttccgat ctagttgcgg atgggggggg gghn                          44
```